US012742767B2

(12) United States Patent
Li et al.

(10) Patent No.: US 12,742,767 B2
(45) Date of Patent: Sep. 22, 2026

(54) ROBOT SYSTEM AND METHOD FOR MONITORING FARMLAND NITROGEN LEACHING

(71) Applicant: Agricultural Information Institute of CAAS, Beijing (CN)

(72) Inventors: Xian Li, Beijing (CN); Xiangnan He, Beijing (CN); Rui Yan, Beijing (CN); Zhen Wang, Beijing (CN); Zhemin Li, Beijing (CN)

(73) Assignee: Agricultural Information Institute of CAAS, Beijing (CN)

( * ) Notice: Subject to any disclaimer, the term of this patent is extended or adjusted under 35 U.S.C. 154(b) by 235 days.

(21) Appl. No.: 18/534,496

(22) Filed: Dec. 8, 2023

(65) Prior Publication Data

US 2024/0426801 A1 Dec. 26, 2024

(30) Foreign Application Priority Data

Jun. 26, 2023 (CN) ........................ 202310753705.X

(51) Int. Cl.
*G01N 33/24* (2006.01)
*G01N 1/00* (2006.01)
(Continued)

(52) U.S. Cl.
CPC ............... *G01N 33/24* (2013.01); *G01N 1/08* (2013.01); *G01N 1/16* (2013.01); *G01N 1/4055* (2013.01);
(Continued)

(58) Field of Classification Search
CPC ....... B25J 11/00; G01C 21/005; G01D 21/02; G01N 1/08; G01N 1/16; G01N 1/4055; G01N 2001/002; G01N 2001/021; G01N 2001/1025; G01N 2001/4061; G01N 33/00; G01N 33/0003; G01N 33/24;
(Continued)

(56) References Cited

U.S. PATENT DOCUMENTS

2003/0112152 A1* 6/2003 Pickett ..................... G01N 1/08 340/870.07
2017/0177938 A1* 6/2017 Papanikolopoulos ....................... G06V 20/17
(Continued)

FOREIGN PATENT DOCUMENTS

CN 108562325 A * 9/2018 ............... C22B 3/04
CN 110398575 A * 11/2019 ............... G01N 1/14
(Continued)

*Primary Examiner* — David L Singer
(74) *Attorney, Agent, or Firm* — Keller Preece PLLC

(57) ABSTRACT

The present disclosure discloses a robot system and method for monitoring farmland nitrogen leaching. The robot system includes a cloud platform, a monitoring robot, and a leachate collection module. The cloud platform is configured to send information about a to-be-measured site and a to-be-measured depth to the monitoring robot and receive measurement information of the monitoring robot; and the monitoring robot is configured to move to the to-be-measured site to be connected to the leachate collection module at the to-be-measured depth of the to-be-measured site, extract a leachate of the leachate collection module, perform leachate nitrogen detection on the leachate, and send a leachate nitrogen detection result to the cloud platform.

8 Claims, 5 Drawing Sheets

(51) Int. Cl.

| | |
|---|---|
| ***G01N 1/02*** | (2006.01) |
| ***G01N 1/08*** | (2006.01) |
| ***G01N 1/10*** | (2006.01) |
| ***G01N 1/16*** | (2006.01) |
| ***G01N 1/40*** | (2006.01) |
| ***G01W 1/04*** | (2006.01) |
| ***G05D 1/225*** | (2024.01) |
| ***G05D 1/226*** | (2024.01) |
| ***G05D 1/229*** | (2024.01) |
| ***G05D 1/248*** | (2024.01) |
| ***G05D 1/43*** | (2024.01) |
| ***G05D 1/656*** | (2024.01) |
| ***G05D 107/20*** | (2024.01) |
| ***G05D 109/10*** | (2024.01) |
| ***G05D 111/30*** | (2024.01) |

(52) U.S. Cl.

CPC .............. *G01W 1/04* (2013.01); *G05D 1/225* (2024.01); *G05D 1/2265* (2024.01); *G05D 1/229* (2024.01); *G05D 1/248* (2024.01); *G05D 1/43* (2024.01); *G05D 1/656* (2024.01); *G01N 2001/002* (2013.01); *G01N 2001/021* (2013.01); *G01N 2001/1025* (2013.01); *G01N 2001/4061* (2013.01); *G01N 33/245* (2024.05); *G05D 2107/21* (2024.01); *G05D 2109/10* (2024.01); *G05D 2111/30* (2024.01)

(58) Field of Classification Search

CPC ....... G01N 33/245; G01W 1/04; G05D 1/225; G05D 1/2265; G05D 1/229; G05D 1/247; G05D 1/248; G05D 1/43; G05D 1/656; G05D 2105/89; G05D 2107/21; G05D 2109/10; G05D 2111/30; H04L 67/10; H04L 67/12; H04Q 9/00

See application file for complete search history.

(56) References Cited

U.S. PATENT DOCUMENTS

| | | | | |
|---|---|---|---|---|
| 2019/0101505 | A1* | 4/2019 | Liu | G01N 1/08 |
| 2020/0128721 | A1* | 4/2020 | Lewis | G01N 33/24 |
| 2020/0132655 | A1* | 4/2020 | Kusiek | G01N 27/333 |

FOREIGN PATENT DOCUMENTS

| | | | | | |
|---|---|---|---|---|---|
| CN | 216050939 | U | * | 3/2022 | G01N 1/14 |
| CN | 115753242 | A | * | 3/2023 | G01N 1/14 |
| CN | 115754245 | A | * | 3/2023 | G01N 1/14 |

* cited by examiner

ROBOT SYSTEM AND METHOD FOR MONITORING FARMLAND NITROGEN LEACHING

CROSS REFERENCE TO RELATED APPLICATION

This patent application claims the benefit and priority of Chinese Patent Application No. 202310753705.X, filed with the China National Intellectual Property Administration on Jun. 26, 2023, the disclosure of which is incorporated by reference herein in its entirety as part of the present application.

TECHNICAL FIELD

The present disclosure relates to ecological environment protection technologies, and in particular, to a robot system and method for monitoring farmland nitrogen leaching.

BACKGROUND

Nitrogen is a necessary nutritive element in a plant growth process, and has a great significant effect on growth and development of crops. Therefore, in agricultural production, farmers supplement missing nitrogen elements in soil by using chemical fertilizers to improve a yield and quality of the crops. However, nitrogen components in the chemical fertilizer cannot be completely absorbed and used by plants, and a part of nitrogen enters groundwater with scouring of rainwater and irrigation water and flowing and leakage of groundwater, resulting in excessive nitrogen content in the groundwater and causing environmental and health problems.

Currently, an agricultural nitrogen leaching problem has aroused extensive attention. According to a result of a soil pollution survey in China, nitrogen pollution in farmland soil is one of the main types of national soil pollution, with about ¼ of farmland soil having the nitrogen pollution problem. In addition, due to the nitrogen leaching problem, the excessive nitrogen content in the groundwater has also become one of the important problems in current environmental protection. According to statistics, more than ⅓ of regions have the excessive nitrogen content in national groundwater, with main distribution regions being the eastern region and the northern plain region.

Nitrogen pollution not only causes serious harm to human health and ecological environment, but also brings a great challenge to agricultural production and quality of agricultural products. Excessive nitrogen content leads to excessive toxin content in the agricultural products, seriously affecting health and safety of people. In addition, great loss of nitrogen also causes loss of soil fertility, resulting in land degradation and reduced quality of cultivated land.

Therefore, resolving the nitrogen leaching problem has become one of the important tasks in current environmental protection and agricultural production. An intelligent farmland nitrogen leaching monitoring system is established, the excessive nitrogen content can be found and processed in time, farmers are assisted in scientific fertilization, loss and pollution of nitrogen are reduced, groundwater resources and sustainable development of the ecological environment are protected.

A conventional nitrogen leachate monitoring method generally includes a static leachate collection method, a dynamic leaching method, a rhizospheric liquid collection method, a micro soil column leaching method, and a sampling leaching method.

1. The static leachate collection method means that a leachate collection apparatus is arranged in farmland, a leachate sample is collected for a specific period of time, and then nitrogen content in the leachate sample is detected and analyzed. According to the method, the collection apparatus needs to be arranged in the farmland, which has a specific impact on soil.
2. The dynamic leaching method is that a specific amount of water is poured into soil through a spraying or seepage apparatus and a water sample obtained through soil leaching is collected and analyzed. According to the method, the operation is complex, and an irrigation apparatus and a collection apparatus need to be arranged, with relatively high costs.
3. The rhizospheric liquid collection method is that a rhizospheric liquid sampling tube is arranged through manual excavation, a rhizospheric liquid sample is collected from rhizospheric soil, and then nitrogen content in the sample is detected and analyzed. According to the method, the operation is complex, and the sampling tube needs to be arranged through excavation, with high costs.
4. The micro soil column leaching method is that a collected soil sample is filled in a micro soil column, then a specific amount of water is poured into the soil column through a spraying or seepage apparatus, and a water sample obtained through soil column leaching is collected and analyzed. According to the method, a large quantity of soil samples are required, and the operation is complex.
5. The sampling leaching method is that a soil sample is placed in a leaching apparatus, a specific amount of water is added to the soil sample, and then a leachate is collected and analyzed. The method has significant damage to the soil and is prone to secondary pollution.

Therefore, the current nitrogen leaching monitoring method generally adopts a method of combining on-site sampling and laboratory analysis, which consumes time and effort and cannot implement real-time detection. A small part of the nitrogen leaching monitoring method adopts a fixed detection method. According to the method, after a large-volume leaching barrel is mounted at a fixed sampling point, a leachate is extracted, and the leachate is transported to a leachate detection terminal through a pipeline for nitrogen leaching monitoring, and a plurality of large-volume leaching barrels and pipelines need to be laid at a plurality of sampling points with high preliminary construction costs, great damage to a soil environment, and a complex processing process.

SUMMARY

To resolve the technical problems that in an existing technology, the nitrogen leaching monitoring method generally adopts a method of combining on-site sampling and laboratory analysis, which consumes time and effort and cannot implement real-time detection, and a small part of the nitrogen leaching monitoring method adopts a fixed detection method, according to the method, after a large-volume leaching barrel is mounted at a fixed sampling point, a leachate is extracted, and the leachate is transported to a leachate detection terminal through a pipeline for nitrogen leaching monitoring, so that a plurality of large-volume leaching barrels and pipelines need to be laid at a plurality of sampling points with high preliminary construction costs, great damage to a soil environment, and a complex processing process, the present disclosure provides a robot system and method for monitoring farmland nitrogen leaching. The robot system completes multi-site and multi-depth leachate automatic extraction in a large range of farmland soil in a movable manner, and intelligently detects and analyzes the extracted leachate in real time in a full process without depending on manual collection and laboratory analysis.

To achieve the above objectives, the present disclosure adopts the following technical solutions.

A robot system for monitoring farmland nitrogen leaching is provided. The robot system includes a cloud platform, a monitoring robot, and a leachate collection module.

The cloud platform is configured to send information about a to-be-measured site and a to-be-measured depth to the monitoring robot and receive measurement information of the monitoring robot.

The monitoring robot is configured to move to the to-be-measured site to be connected to the leachate collection module at the to-be-measured depth of the to-be-measured site, extract a leachate of the leachate collection module, perform leachate nitrogen detection on the leachate, and send a leachate nitrogen detection result to the cloud platform.

In addition, in the robot system for monitoring farmland nitrogen leaching in the present disclosure, there are a plurality of to-be-measured sites, and each to-be-measured site includes one or more to-be-measured depths; the cloud platform includes a path planning unit, and the path planning unit plans a detection moving track of the monitoring robot according to a position relationship among the plurality of to-be-measured sites and a quantity of to-be-measured depths of each to-be-measured site, and sends the detection moving track to the monitoring robot; and the monitoring robot receives the detection moving track, and sequentially performs leachate nitrogen detection at each to-be-measured site and each to-be-measured depth according to the detection moving track.

In addition, the robot system for monitoring farmland nitrogen leaching in the present disclosure, the leachate collection module is provided at the to-be-measured depth of the to-be-measured site, and the leachate collection module includes a leachate collection system, an electromagnetic valve module, a transmission branch pipeline, and a Zigbee® (wireless ad hoc network) module; and the leachate collection system is configured to collect a leachate at the to-be-measured depth of the to-be-measured site, the electromagnetic valve module is connected to the leachate collection system and the transmission branch pipeline, and the Zigbee® module is connected to the electromagnetic valve module and is connected to a Zigbee® base station module of the monitoring robot in a wireless manner and is configured to open or close the electromagnetic valve module according to an instruction sent by the Zigbee® base station module.

In addition, in the robot system for monitoring farmland nitrogen leaching in the present disclosure, the monitoring robot includes the Zigbee® base station module, a leachate pipeline docking module, and a leachate extraction driving module; the to-be-measured site includes one or more to-be-measured depths, and the leachate collection module is provided at each to-be-measured depth, and the leachate collection module includes a leachate collection system, an electromagnetic valve module, a transmission branch pipeline, and a Zigbee® module; and the monitoring robot includes the Zigbee® base station module that is in wireless connection with the Zigbee® module of the leachate collection module at each to-be-measured depth and the leachate pipeline docking module that is connected to the transmission branch pipeline of the leachate collection module at each to-be-measured depth; and the monitoring robot is configured to communicate with the Zigbee® module of the leachate collection module at each to-be-measured depth through the Zigbee® base station module, open the electromagnetic valve module of the leachate collection module at each to-be-measured depth, extract a leachate from the transmission branch pipeline of the leachate collection module at each to-be-measured depth, and perform leachate nitrogen detection at each to-be-measured depth; and when a leachate at one to-be-measured depth is extracted, only an electromagnetic valve module of a leachate collection module at the to-be-measured depth is opened, and an electromagnetic valve module of a leachate collection module at another to-be-measured depth is kept in a closed state.

In addition, in the robot system for monitoring farmland nitrogen leaching in the present disclosure, the monitoring robot includes a movable module, the movable module includes a navigation module, a movable carrier, and a movable carrier driving unit, the navigation module is configured to detect a position of the monitoring robot, the movable carrier includes a wheel-type movable platform and a motor, and the movable carrier driving unit is configured to control a moving direction and a moving distance of the movable carrier.

In addition, in the robot system for monitoring farmland nitrogen leaching in the present disclosure, the monitoring robot includes an environment sensing module, the environment sensing module includes a temperature and humidity sensor, a wind direction sensor, a rainfall sensor, and a light intensity sensor, and the monitoring robot sends information about a temperature, humidity, a wind direction, a rainfall, and light intensity collected by the environment sensing module to the cloud platform together with the leachate nitrogen detection result.

In addition, in the robot system for monitoring farmland nitrogen leaching in the present disclosure, there are a plurality of to-be-measured sites, each to-be-measured site includes one or more to-be-measured depths, the leachate collection module is provided at each to-be-measured depth of each to-be-measured site, and the leachate collection module includes a leachate collection system, a leachate liquid level sensor, an electromagnetic valve module, a transmission branch pipeline, and a Zigbee® module; and the leaching monitoring robot includes a Zigbee® base station module and a path planning unit;

after receiving the plurality of to-be-measured sites and information about one or more to-be-measured depths of each to-be-measured site, the leaching monitoring robot sends a start command to the Zigbee® module of the leachate collection module at each to-be-measured depth of each to-be-measured site through the Zigbee® base station module, and the leachate liquid level sensor of the leachate collection module at each to-be-measured depth of each to-be-measured site detects a liquid level of a leachate collected by a leachate collection system corresponding to the leachate collection module, and sends the liquid level of the leachate collected by the leachate collection system corresponding to the leachate collection module to the leaching monitoring robot according to a predetermined period through the Zigbee® module at each to-be-measured depth of each to-be-measured site; and a dynamical path planning unit of the leaching monitoring robot dynamically plans a detection moving track of the monitoring robot according to a liquid level of a leachate collected by each leachate collection system, a position relationship among the to-be-measured sites, and a quantity of to-be-measured depths of each to-be-measured site and according to each predetermined period; and the monitoring robot performs leachate extraction and leachate nitrogen detection at each to-be-measured site and each to-be-measured depth according to the dynamically planned detection moving track.

In addition, in the robot system for monitoring farmland nitrogen leaching in the present disclosure, the monitoring robot includes a micro-fluidic module, a leachate nitrogen detection module, a cleaning module, a waste liquid processing module, and a data processing module, the micro-fluidic module adds a to-be-reacted chemical reagent to the extracted leachate, and supplies a mixture of the chemical reagent and the leachate to the leachate nitrogen detection module for leachate nitrogen detection, the cleaning module is configured to clean the micro-fluidic module and the leachate nitrogen detection module in the monitoring robot through cleaning liquid after leachate nitrogen detection is completed once; and the waste liquid processing module is configured to discharge the mixture of the chemical reagent and the leachate and the cleaning liquid.

A method for monitoring farmland nitrogen leaching includes the following steps:

A: sending, by a cloud platform, information about a to-be-measured site and a to-be-measured depth to a monitoring robot; and B: moving, by the monitoring robot, to the to-be-measured site to be connected to a leachate collection module at the to-be-measured depth of the to-be-measured site, where one or more leachate collection modules at one to-be-measured site are referred to as a to-be-measured node. The monitoring robot extracts a leachate of the leachate collection module, performs leachate nitrogen detection on the leachate, and sends a leachate nitrogen detection result to the cloud platform.

In addition, in the method for monitoring farmland nitrogen leaching in the present disclosure, in step A, there are a plurality of to-be-measured sites sent by the cloud platform to the monitoring robot, and each to-be-measured site includes one or more to-be-measured depths; and in step B, the moving, by the monitoring robot, to the to-be-measured site for leachate extraction and leachate nitrogen detection includes:

after receiving the plurality of to-be-measured sites and information about one or more to-be-measured depths of each to-be-measured site, sending, by the leaching monitoring robot, a start command to a Zigbee® module of a leachate collection module at each to-be-measured depth of each to-be-measured site through a Zigbee® base station module, and detecting, by a leachate liquid level sensor of the leachate collection module at each to-be-measured depth of each to-be-measured site, a liquid level of a leachate collected by a leachate collection system corresponding to the leachate collection module, and sending the liquid level of the leachate collected by the leachate collection system corresponding to the leachate collection module to the leaching monitoring robot according to a predetermined period through the Zigbee® module at each to-be-measured depth of each to-be-measured site; and dynamically planning, a dynamical path planning unit of the leaching monitoring robot, a detection moving track of the monitoring robot according to a liquid level of a leachate collected by each leachate collection system, a position relationship among the to-be-measured sites, and a quantity of to-be-measured depths of each to-be-measured site and according to each predetermined period; and performing, by the monitoring robot, leachate extraction and leachate nitrogen detection at each to-be-measured site and each to-be-measured depth according to the dynamically planned detection moving track.

The present disclosure has the following technical effects.

1. According to the farmland nitrogen leaching monitoring robot and method in the present disclosure, a large-range multi-point underground leachate can be automatically obtained and intelligently detected and analyzed.
2. The leaching monitoring robot in the present disclosure can perform autonomous navigation and move to each to-be-measured site to perform leachate collection and leachate nitrogen analysis, so that one or more leachate nitrogen analysis apparatuses do not need be designed at each to-be-measured site, and each to-be-measured site shares one monitoring robot, so as to ensure consistency of leachate nitrogen analysis at each to-be-measured site and each to-be-measured depth, avoid individual difference between each test device, thereby improving accuracy. In addition, the costs of the entire system can be reduced, and investment of a large quantity of leachate nitrogen analysis apparatuses can be avoided. In addition, because each leachate nitrogen analysis apparatus needs to report test result information to the cloud platform, but in the present disclosure, all tasks are uniformly completed by the monitoring robot, so that power consumption can be saved, and circuit wiring for each to-be-measured site can be avoided.
3. The leaching monitoring robot in the present disclosure adopts a micro-fluidic technology before a leachate nitrogen detection module, so that a nitrogen component in a leachate can be detected by extracting a small amount of leachate, thereby avoiding consumption of a large amount of time for extracting a large amount of leachate for nitrogen measurement at a plurality of to-be-measured depths of a plurality of to-be-measured sites.
4. According to the robot system and method for monitoring farmland nitrogen leaching in the present disclosure, quick collection, detection, and analysis of a plurality of leaching monitoring nodes on a large range can be implemented. Unattended monitoring can be implemented by setting a base station control program. A small amount of leachate is collected by using the micro-fluidic module. The costs are low, a detection time is short, efficiency is high, and a degree of automation and intelligence is high.
5. In particular, to further improve test efficiency, according to the robot system and method for monitoring farmland nitrogen leaching in the present invention, a dynamic path planning method is also adopted. A detection moving track of the monitoring robot is dynamically planned according to a liquid level of a leachate collected by each leachate collection system, a position relationship among to-be-measured sites, and a quantity of to-be-measured depths of each to-be-measured site and according to each predetermined period without presetting the detection moving track. After each to-be-measured site is measured, a next to-be-measured site is dynamically calculated and path optimization is performed according to a step method, so as to avoid a waiting time for leachate collection at a to-be-measured site. Therefore, it greatly improves the entire system test efficiency of the robot system and method for monitoring farmland nitrogen leaching for a plurality of to-be-measured sites and a plurality of to-be-measured depths.

DETAILED DESCRIPTION OF THE EMBODIMENTS

Figure 1:
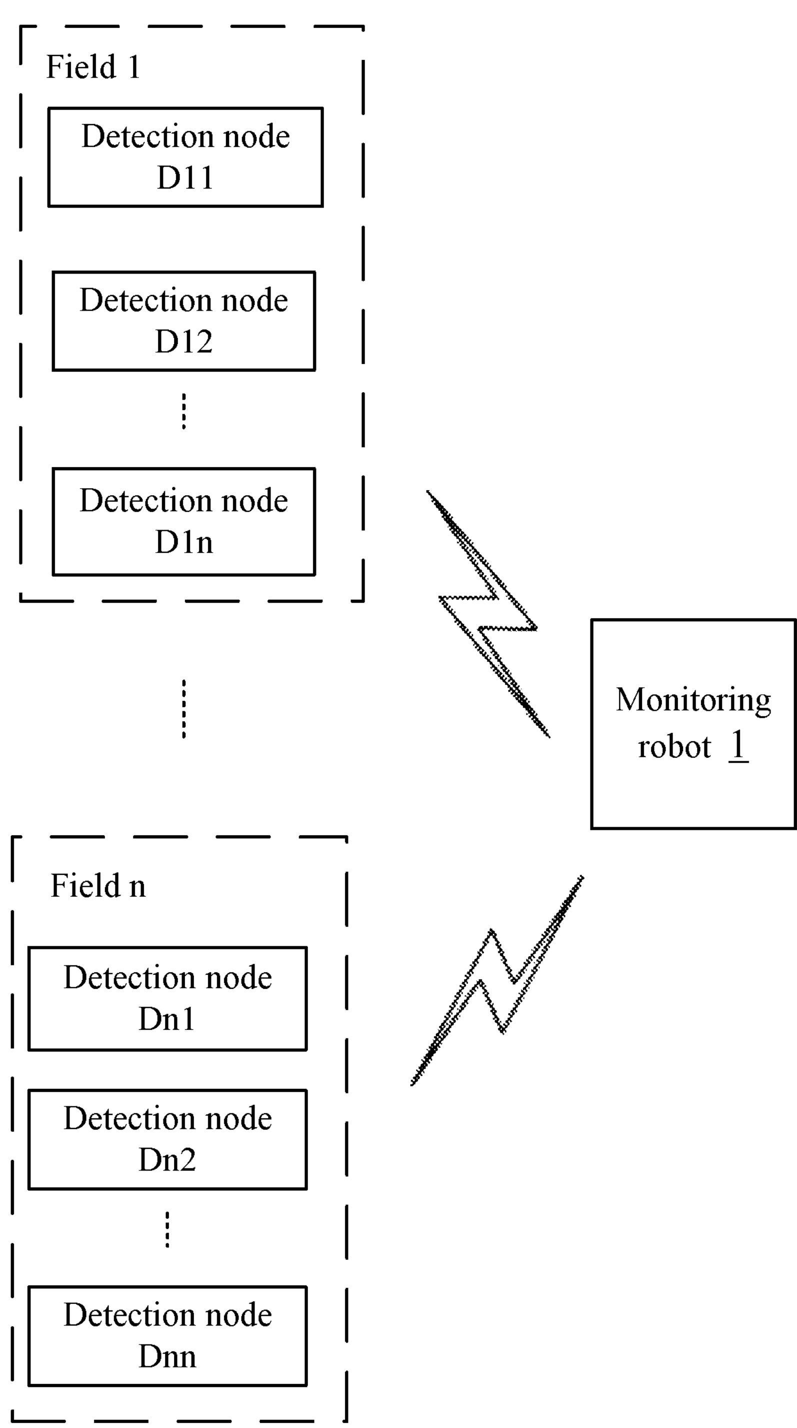
FIG. 1 is a schematic structural diagram of a robot system for monitoring farmland nitrogen leaching according to a specific implementation of the present disclosure.

The present disclosure will be explained in detail below with reference to the accompanying drawings.

Detailed exemplary embodiments are disclosed below. However, the specific structure and functional details disclosed herein are only for the purpose of describing the exemplary embodiments.

However, it should be understood that the present disclosure is not limited to the disclosed specific exemplary embodiments, but covers all modifications, equivalents, and substitutions falling within the scope of the present disclosure. In descriptions of all the accompanying drawings, the same reference numerals indicate the same elements.

The structure, scale, size, and the like shown in the drawings of this specification are only used to match the content disclosed in the specification and for those skilled in the art to understand and read, which are not used to limit the limitations for implementing the present disclosure and thus are not technically substantial. Any structural modification, scaling relation change, or size adjustment made without affecting the effects and objectives that can be achieved by the present disclosure should fall within the scope that can be encompassed by the technical content disclosed in the present disclosure. In addition, position limit words in this specification are only for the sake of clarity and are not intended to limit the application scope of the present disclosure, and the change or adjustment of the relative relations shall be deemed as falling within the applicable scope of the present disclosure without substantial alteration of technical contents.

In addition, it should be understood that the term "and/or" as used herein includes any and all combinations of one or more related listed items. In addition, it should be understood that when a component or unit is referred to as "connected" or "coupled" to another component or unit, the component or unit may be directly connected or coupled to another component or unit, or there may be an intermediate component or unit. In addition, another word used to describe a relationship between components or units should be understood in a same way (for example, "between" corresponds to "direct between", and "adjacent" corresponds to "direct adjacent").

Figure 2:
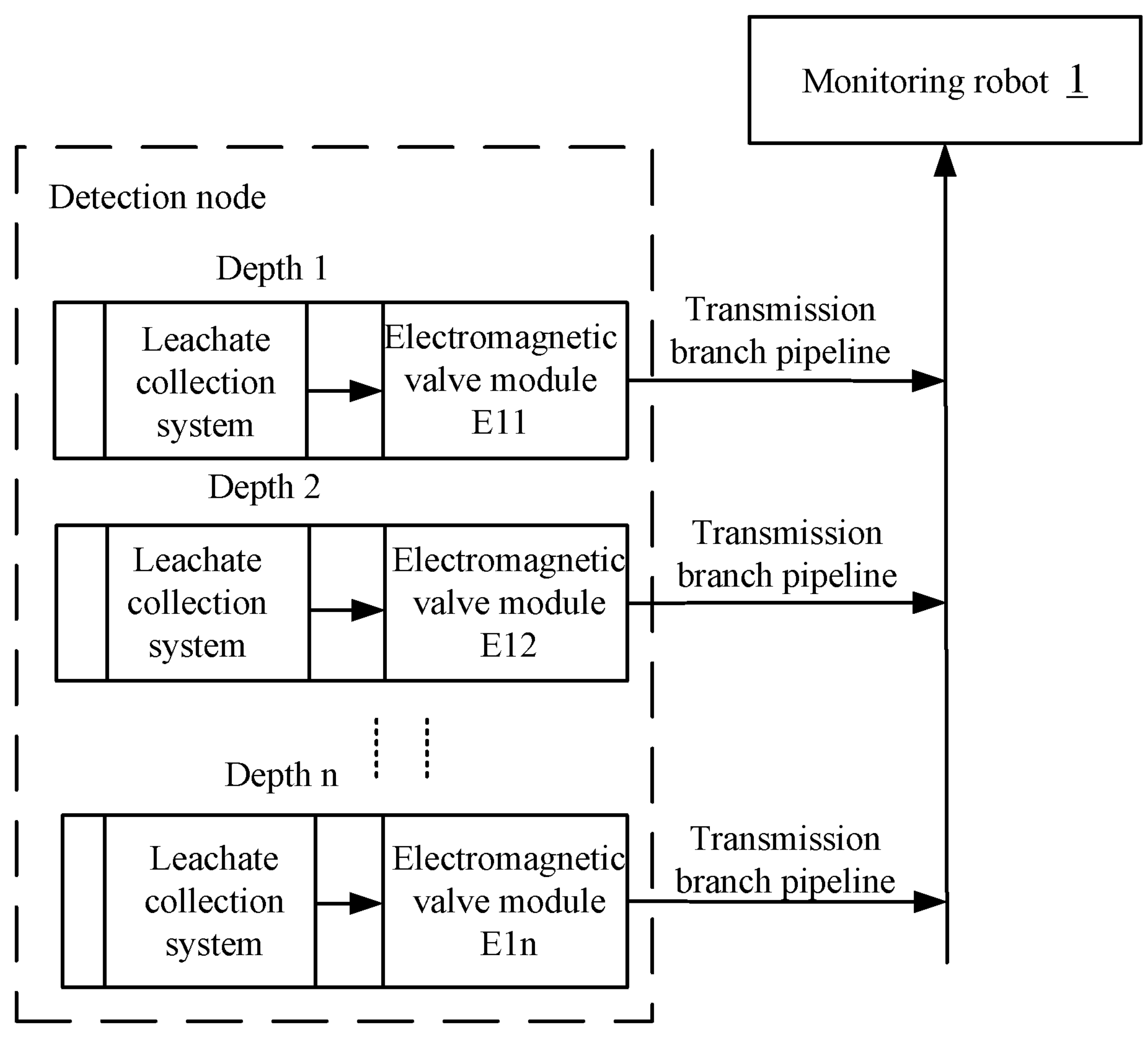
FIG. 2 is a schematic structural diagram of a robot system for monitoring farmland nitrogen leaching according to a specific implementation of the present disclosure.
Figure 3:
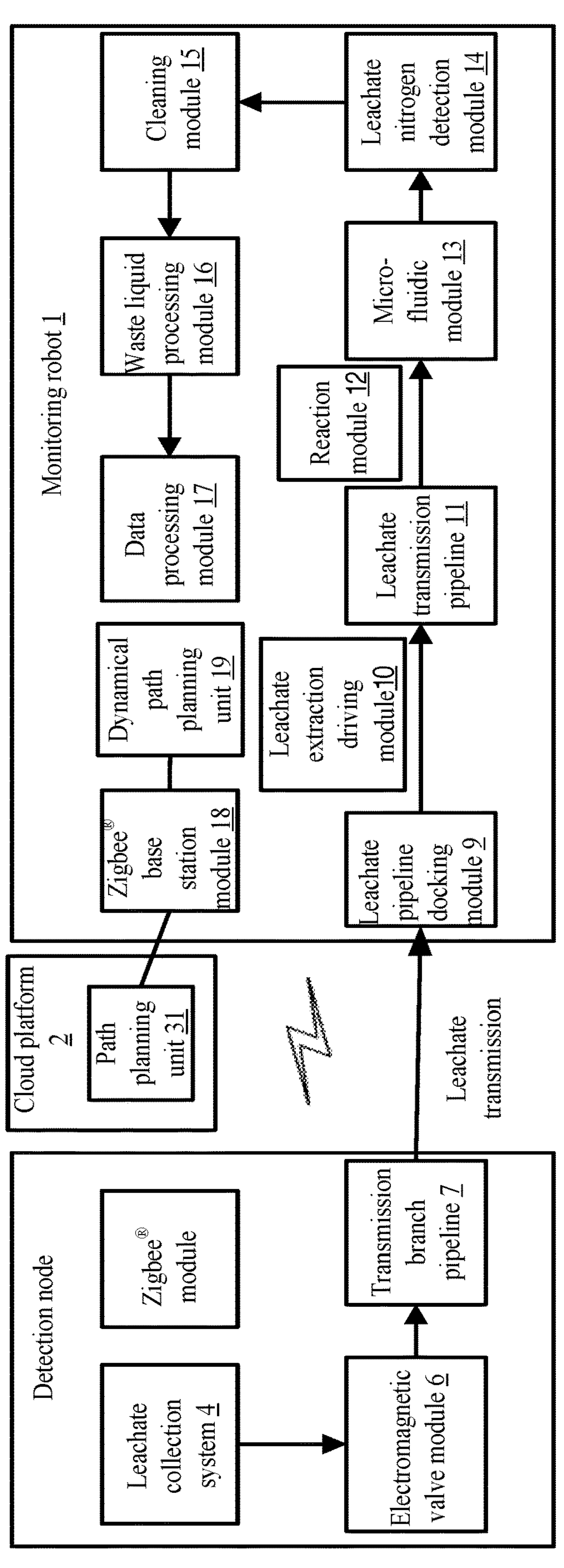
FIG. 3 is a schematic structural diagram of a robot system for monitoring farmland nitrogen leaching according to a specific implementation of the present disclosure.

FIG. 1 to FIG. 3 are all schematic structural diagrams of a robot system for monitoring farmland nitrogen leaching according to a specific implementation of the present disclosure. As shown in the figures, the following technical solutions are adopted in the specific implementations of the present disclosure.

First, management personnel of a cloud platform 2 sets information about a plurality of to-be-measured site and to-be-measured depths according to a test requirement, where each to-be-measured site is used as a to-be-measured node (D11, D12, . . . , D1n; . . . ; Dn1, Dn2, . . . , Dnn); and sends the information to a monitoring robot 1. The monitoring robot receives the information of the cloud platform through a narrowband Internet of Things (NB-IoT) communication module, and parses the information of the cloud platform.

The monitoring robot receives path information planned by a path planning unit of the cloud platform, drives a movable carrier to drive the monitoring robot to move, determines a real-time position through a positioning module in a moving process, and sends information about the real-time position to the cloud platform through the NB-IoT module. After the monitoring robot reaches a position of a to-be-measured site, a leachate pipeline docking module 9 of the monitoring robot is connected to a leachate collection module 3 at a to-be-measured depth of the to-be-measured site and.

Each to-be-measured site may include a plurality of to-be-measured depths, and the leachate collection module is provided at each to-be-measured depth. One or more leachate collection modules at each to-be-measured site are collectively referred to as a to-be-measured node. Each leachate collection module includes an electromagnetic valve module (E11, E12, . . . , E1n). Each leachate collection module opens the electromagnetic valve module of the leachate collection module according to an instruction of the monitoring robot. A control module of the monitoring robot extracts a leachate in the leachate collection module to a leachate storage unit that temporarily stores the leachate in the monitoring robot, and timely adjusts, according to information of a transmission sensing unit, a water pump rate for extracting the leachate.

After extracting the leachate, the leaching monitoring robot sends an electromagnetic valve module close command to the leachate collection module through a Zigbee® (wireless ad hoc network) base station module, and starts to drive a leachate monitoring unit to perform leachate nitrogen detection. After the leaching monitoring robot completes leachate nitrogen monitoring at a first depth, the monitoring robot sends an electromagnetic valve module open command to a leachate collection module at a next depth again, and repeats the action until leachate extraction and leachate nitrogen analysis at all depths of the site are completed.

After completing all detection tasks of the to-be-measured site, the monitoring robot obtains, through an environment sensing control unit, environment information collected by an environment sensing unit, and finally uploads the obtained environment information of the site and leachate nitrogen information of each depth to the cloud platform. The monitoring robot starts to plan a moving route to determine a next to-be-measured site, automatically moves to the to-be-measured site, and repeats the action of monitoring the first to-be-measured site until all detection tasks are completed. The cloud platform receives and stores the information uploaded by the monitoring robot.

To implement the foregoing operations, the monitoring robot includes a movable module, an environment sensing module, a leachate nitrogen detection module, a wireless communication module, a power supply module, a microprocessor module, a control circuit board, a leachate transmission module, and a navigation module. The movable module includes a movable carrier and a movable carrier driving module. The environment sensing module includes a temperature and humidity sensor, a wind direction sensor, a rainfall sensor, and a light intensity sensor. The leachate nitrogen detection module includes a micro-fluidic chip module, a leachate nitrogen detection module, a cleaning module, a waste liquid processing module, and a data processing module. The wireless communication module includes a wireless communication chip module (an NB-IoT wireless communication module and a Zigbee® base station module) and a wireless communication data storage module. The power supply module includes a solar energy power supply module and a lithium battery power supply module. The leachate transmission module includes a leachate transmission pipeline 11, a leachate extraction driving module 10, and a leachate pipeline docking module 9. The navigation module includes a Beidou positioning module and an attitude sensor module. The leachate pipeline docking module may be connected to a transmission branch pipeline at each to-be-measured depth of each to-be-measured site.

A process in which the monitoring robot is connected to the leachate collection module is that the monitoring robot sends a connection command to the leachate collection module through the Zigbee® base station communication module, where the leachate collection module includes a Zigbee® wireless communication module 8, an electromagnetic valve module 6, a transmission branch pipeline 7, and a leachate collection system 4, the monitoring robot is connected to the transmission branch pipeline of the leachate collection module through the leachate pipeline docking module, and the monitoring robot sends an electromagnetic valve module open command to each leachate collection module at each to-be-measured site according to a measurement command. After extracting the leachate, the robot sends an electromagnetic valve module close command and cleans the leachate transmission pipeline.

After completing a task of analyzing nitrogen content in the leachate, the monitoring robot sends an electromagnetic valve module open command again, and an electromagnetic valve module of a next leachate collection module is opened. The robot repeats the process of extracting and analyzing the leachate and sending an electromagnetic valve control command until leachate at all to-be-measured depths of the to-be-measured site are extracted, detected, and analyzed. The robot moves to a next to-be-measured site according to an indication of the path planning unit of the cloud platform, to repeat the foregoing actions. The actions and a matching relationship are shown in FIG. 1 and FIG. 2.

The leachate extraction and detection process is shown in FIG. 2. The monitoring robot extracts a small amount of leachate to a front end of the micro-fluidic module through the leachate transmission pipeline, after being mixed with a to-be-reacted chemical reagent, the leachate enters a leachate nitrogen detection module through the micro-fluidic module, nitrogen detection in mixed liquid is completed, and a sensing curve of leachate nitrogen is obtained. Sensing data of the leachate nitrogen is converted into nitrogen content in the leachate through the data processing module.

Therefore, a specific implementation of the present disclosure provides a robot system for monitoring farmland nitrogen leaching. The robot system includes a cloud platform, a monitoring robot, and a leachate collection module.

The cloud platform is configured to send information about a to-be-measured site and a to-be-measured depth to the monitoring robot and receive measurement information of the monitoring robot.

The monitoring robot is configured to move to the to-be-measured site to be connected to the leachate collection module at the to-be-measured depth of the to-be-measured site, extract a leachate of the leachate collection module, perform leachate nitrogen detection on the leachate, and send a leachate nitrogen detection result to the cloud platform. One to-be-measured site may include one or more leachate collection modules, which are collectively referred to as a to-be-measured node.

In addition, in the robot system for monitoring farmland nitrogen leaching in the specific implementation of the present disclosure, there are a plurality of to-be-measured sites, and each to-be-measured site includes one or more to-be-measured depths; the cloud platform includes a path planning unit 31, and the path planning unit 31 plans a detection moving track of the monitoring robot according to a position relationship among the plurality of to-be-measured sites and a quantity of to-be-measured depths of each to-be-measured site, and sends the detection moving track to the monitoring robot; and the monitoring robot receives the detection moving track, and sequentially performs leachate nitrogen detection at each to-be-measured site and each to-be-measured depth according to the detection moving track.

In addition, the robot system for monitoring farmland nitrogen leaching in the specific implementation of the present disclosure, the leachate collection module is provided at the to-be-measured depth of the to-be-measured site, and the leachate collection module includes a leachate collection system, an electromagnetic valve module, a transmission branch pipeline, and a Zigbee® module; and the leachate collection system is configured to collect a leachate at the to-be-measured depth of the to-be-measured site, the electromagnetic valve module is connected to the leachate collection system and the transmission branch pipeline, and the Zigbee® module is connected to the electromagnetic valve module and is connected to a Zigbee® base station module of the monitoring robot in a wireless manner and is configured to open or close the electromagnetic valve module according to an instruction sent by the Zigbee® base station module.

In addition, in the robot system for monitoring farmland nitrogen leaching in the specific implementation of the present disclosure, the monitoring robot includes the Zigbee® base station module, a leachate pipeline docking module, and a leachate extraction driving module; the to-be-measured site includes one or more to-be-measured depths, and the leachate collection module is provided at each to-be-measured depth, and the leachate collection module includes a leachate collection system, an electromagnetic valve module, a transmission branch pipeline, and a Zigbee® module.

The monitoring robot includes the Zigbee® base station module that is in wireless connection with the Zigbee® module of the leachate collection module at each to-be-measured depth and the leachate pipeline docking module that is connected to the transmission branch pipeline of the leachate collection module at each to-be-measured depth; and the monitoring robot is configured to communicate with the Zigbee® module of the leachate collection module at each to-be-measured depth through the Zigbee® base station module, open the electromagnetic valve module of the leachate collection module at each to-be-measured depth, extract a leachate from the transmission branch pipeline of the leachate collection module at each to-be-measured depth, and perform leachate nitrogen detection at each to-be-measured depth; and when a leachate at one to-be-measured depth is extracted, only an electromagnetic valve module of a leachate collection module at the to-be-measured depth is opened, and an electromagnetic valve module of a leachate collection module at another to-be-measured depth is kept in a closed state.

In addition, in the robot system for monitoring farmland nitrogen leaching in the specific implementation of the present disclosure, the monitoring robot includes a movable module 20, the movable module includes a navigation module 21, a movable carrier 22, and a movable carrier driving unit 23, the navigation module is configured to detect a position of the monitoring robot, the movable carrier 22 includes a wheel-type movable platform 24 and a motor 25, and the movable carrier driving unit is configured to control a traveling direction and distance of the movable carrier.

In addition, in the robot system for monitoring farmland nitrogen leaching in the specific implementation of the present disclosure, the monitoring robot includes an environment sensing module 26, the environment sensing module includes a temperature and humidity sensor 27, a wind direction sensor 28, a rainfall sensor 29, and a light intensity sensor 30, and the monitoring robot sends information about a temperature, humidity, a wind direction, a rainfall, and light intensity collected by the environment sensing module to the cloud platform together with the leachate nitrogen detection result.

In addition, in the robot system for monitoring farmland nitrogen leaching in the specific implementation of the present disclosure, there are a plurality of to-be-measured sites, each to-be-measured site includes one or more to-be-measured depths, the leachate collection module is provided at each to-be-measured depth of each to-be-measured site, and the leachate collection module includes a leachate collection system 4, a leachate liquid level sensor 5, an electromagnetic valve module 6, a transmission branch pipeline 7, and a Zigbee® module 8; and the leaching monitoring robot includes a Zigbee® base station module 18 and a dynamical path planning unit 19.

After receiving the plurality of to-be-measured sites and information about one or more to-be-measured depths of each to-be-measured site, the leaching monitoring robot sends a start command to the Zigbee® module of the leachate collection module at each to-be-measured depth of each to-be-measured site through the Zigbee® base station module, and the leachate liquid level sensor of the leachate collection module at each to-be-measured depth of each to-be-measured site detects a liquid level of a leachate collected by a leachate collection system corresponding to the leachate collection module, and sends the liquid level of the leachate collected by the leachate collection system corresponding to the leachate collection module to the leaching monitoring robot according to a predetermined period through the Zigbee® module at each to-be-measured depth of each to-be-measured site.

A dynamical path planning unit of the leaching monitoring robot dynamically plans a detection moving track of the monitoring robot according to a liquid level of a leachate collected by each leachate collection system, a position relationship among the to-be-measured sites, and a quantity of to-be-measured depths of each to-be-measured site and according to each predetermined period; and the monitoring robot performs leachate extraction and leachate nitrogen detection at each to-be-measured site and each to-be-measured depth according to the dynamically planned detection moving track.

The foregoing descriptions are the specific implementations of the present disclosure, and the overall test efficiency of the plurality of to-be-measured sites and the plurality of to-be-measured depths is significantly improved. Details are described below.

After the cloud platform sends information about a plurality of to-be-measured sites and one or more to-be-measured depths of each to-be-measured site to the monitoring robot, the monitoring robot first sends the information to a Zigbee® module of a leachate collection module at each of the plurality of to-be-measured depths of the plurality of to-be-measured sites through the Zigbee® base station module. After receiving the information, the Zigbee® module of each leachate collection module opens a respective leachate liquid level sensor. After a liquid level of a leachate collected by each leachate collection system is detected, information about the liquid level of the collected leachate is reported to the monitoring robot through the Zigbee® module of each leachate collection module.

For example, there are six to-be-measured sites in total, which are respectively P1 to P6. P1 to P6 each have three to-be-measured depths, which are denoted as P11 to P13, . . . , and P61 to P63. The leachate collection module is provided at each to-be-measured depth. At a time to, leachate liquid level information of leachate collection modules at three depths of P2 and three depths of P5 is all adequate to meet a measurement requirement, and leachate liquid level information of leachate collection modules at one to-be-measured depth of P1 and one to-be-measured depth of P3 is adequate to meet the measurement requirement. Leachate liquid level information of leachate collection modules at all to-be-measured depths of P4 and P6 is inadequate to meet the measurement requirement. A geographic location of P5 is closer to the monitoring robot, the dynamic path planning unit of the monitoring robot determines to first perform leachate extraction and leachate nitrogen detection at P5 at the moment to. The monitoring robot moves to P5 and performs leachate extraction and leachate nitrogen analysis on leachate collection modules at P51, P52, and P53 in sequence.

When leachate extraction and leachate nitrogen analysis are performed on the leachate collection modules at P51, P52, and P53, two predetermined time intervals such as t1 and t2 have elapsed. At the moment t1 and the moment t2, a Zigbee® module of each leachate collection module continues to report collected leachate liquid level information to the monitoring robot. For example, at the moment t1, a case that the leachate liquid level information of the leachate collection modules at the three depths is adequate to meet the measurement requirement is not implemented at all P1, P3, P4, and P6. At a moment t3, all leachate level information of the leachate collection modules at three depths of P1 is adequate to meet the measurement requirement, and a case that the leachate liquid level information of the leachate collection modules at the three depths is adequate to meet the measurement requirement has not been implemented at the remaining P3, P4, and P6. P1 is closer to P5 than P2. Therefore, after performing leachate extraction and leachate nitrogen analysis on the leachate collection modules at P51, P52, and P53, the monitoring robot selects P1 as a second to-be-measured site, that is, the monitoring robot moves to P1, and performs leachate extraction and leachate nitrogen analysis on the leachate collection modules at P11, P12, and P13 again in sequence.

When leachate extraction and leachate nitrogen analysis are performed on the leachate collection modules at P11, P12, and P13, two predetermined time intervals such as t3 and t4 have elapsed. At the moment t4, the leachate level information of the leachate collection modules at the three depths of each of P4 and P6 is adequate to meet the measurement requirement. The monitoring robot continues to compare a distance between P2, P4, and P6 and P1 and finds that P2 is closest to P1. Therefore, the dynamic path planning unit of the monitoring robot selects P2 as a third to-be-measured site, that is, the monitoring robot moves to P2, and performs leachate extraction and leachate nitrogen analysis on the leachate collection modules at P21, P22, and P23 again in sequence.

Through the dynamic path planning unit, the monitoring robot does not need to wait for leachate collection at a to-be-measured node, or a time for waiting for leachate collection is less. The monitoring robot finds a next to-be-measured site each time in a closest manner, to greatly improve working efficiency of the robot system for monitoring farmland nitrogen leaching.

More specifically, when liquid level depths of the leachate collection modules at not all to-be-measured depths of all the remaining to-be-measured sites are adequate to extract an appropriate amount of leachate, the monitoring robot can compare that liquid level depths of leachate collection modules at several to-be-measured depths of each of the remaining to-be-measured sites are adequate to extract the appropriate amount of leachate, and perform comprehensive determined according to a quantity of leachate collection modules that meet a condition, a sequence, and a distance.

For example, at a time point tn, there are three remaining to-be-measured sites P1, P3, and P6, but when liquid level depths of leachate collection modules at three to-be-measured depths of each of the three to-be-measured sites cannot simultaneously meet a requirement of extracting an appropriate amount of leachate, the monitoring robot considers that P3 is relatively close to a current position, and liquid level depths of leachate collection modules at P31 and P32 have met the requirement. Although P1 is the same as P3, a liquid level depth of the leachate collection module at P11 of P1 does not meet the requirement, and liquid level depths of the leachate collection modules at only P12 and P13 have met the requirement. To avoid the disturbance of a measurement sequence from shallow to deep, the dynamic path planning unit of the monitoring robot selects P3 as a next to-be-measured site.

Alternatively, in another specific implementation, the monitoring robot abandons the measurement sequence from shallow to deep, and pays more attention on a quantity of leachate collection modules that meet the condition and a distance from the current position. The dynamic path planning unit of the monitoring robot may alternatively select P1 at a next to-be-measured site.

Therefore, it can be learned from the specific implementations of the present disclosure that because the monitoring robot has the dynamic path planning unit, the monitoring robot has a high degree of autonomy and can select an optimal manner to implement the entire leachate nitrogen measurement scheme of the plurality of to-be-measured sites and the plurality of to-be-measured depths in combination with a plurality of path optimization policies and considering a plurality of weights.

In addition, in the robot system for monitoring farmland nitrogen leaching in the specific implementation of the present disclosure, the monitoring robot includes a reaction module 12, a micro-fluidic module 13, a leachate nitrogen detection module 14, a cleaning module 15, a waste liquid processing module 16, and a data processing module 17, the micro-fluidic module adds a to-be-reacted chemical reagent to the extracted leachate, and supplies a mixture of the chemical reagent and the leachate to the micro-fluidic module and then to the leachate nitrogen detection module for leachate nitrogen detection, the cleaning module is configured to clean the micro-fluidic module and the leachate nitrogen detection module in the monitoring robot through cleaning liquid after leachate nitrogen detection is completed once; and the waste liquid processing module is configured to discharge the mixture of the chemical reagent and the leachate and the cleaning liquid.

Figure 4:
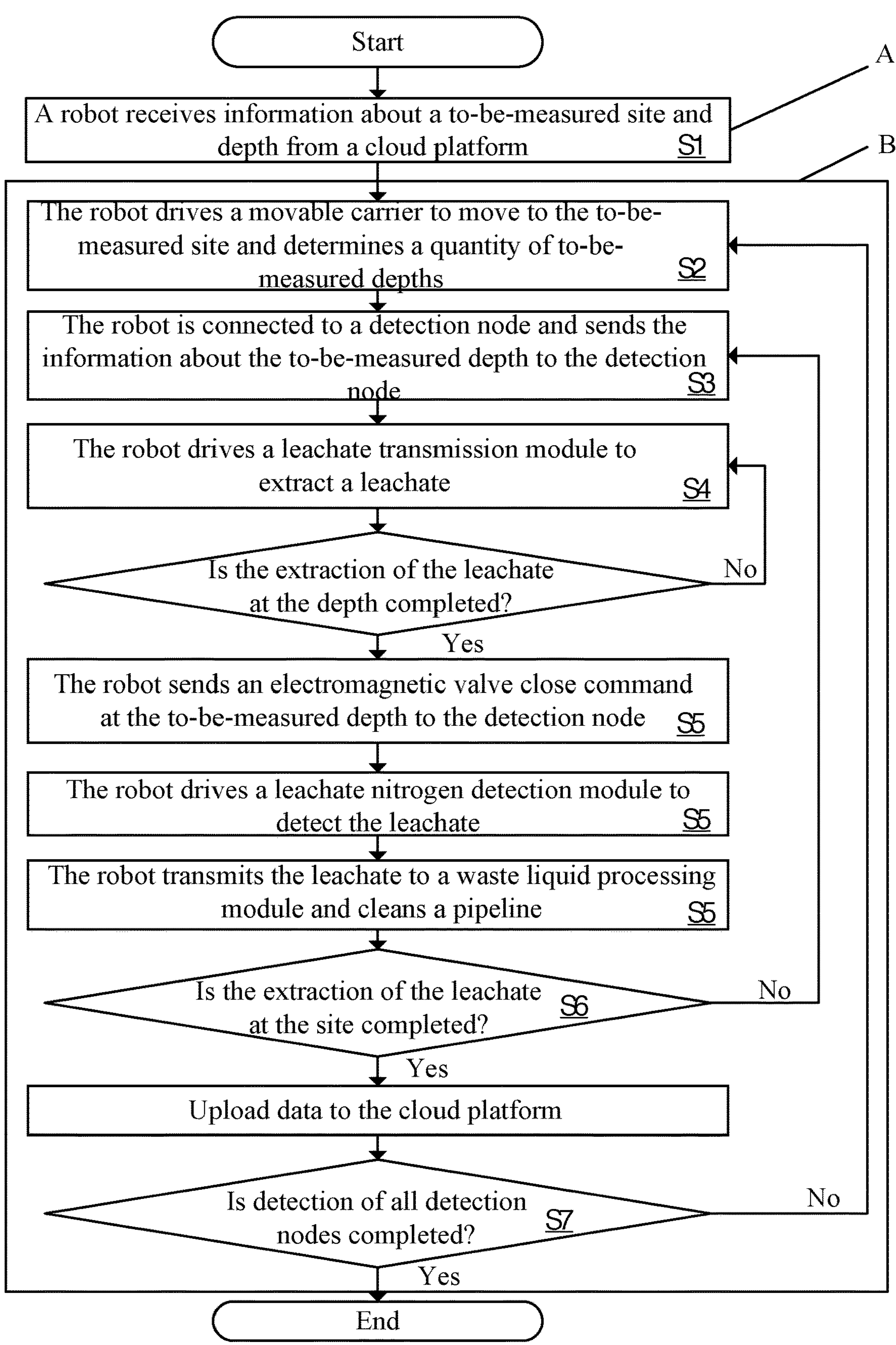
FIG. 4 is a schematic flowchart of a method for monitoring farmland nitrogen leaching according to a specific implementation of the present disclosure.
Figure 5:
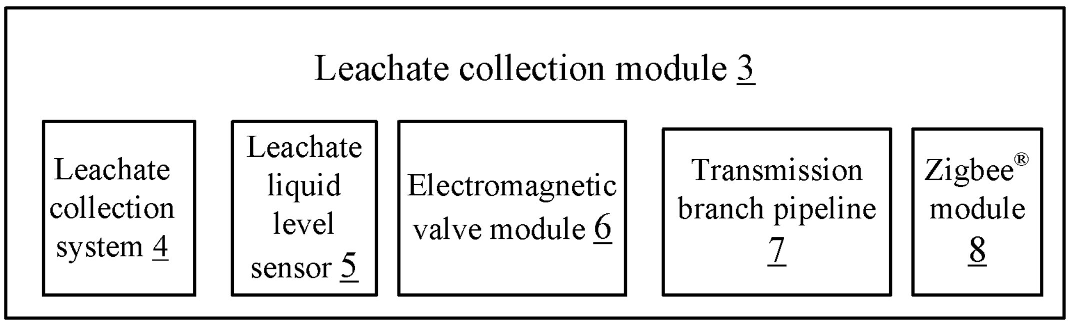
FIG. 5 is a schematic structural diagram of a leachate collection module.
Figure 6:
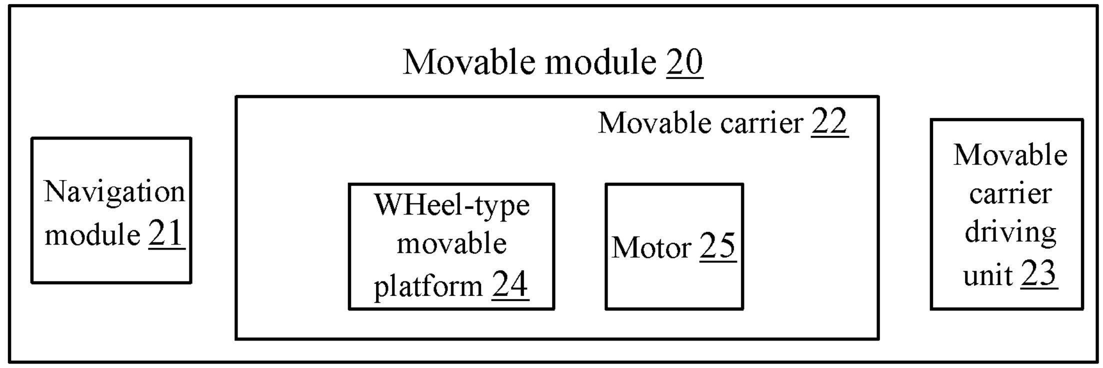
FIG. 6 is a schematic structural diagram of a movable module.
Figure 7:
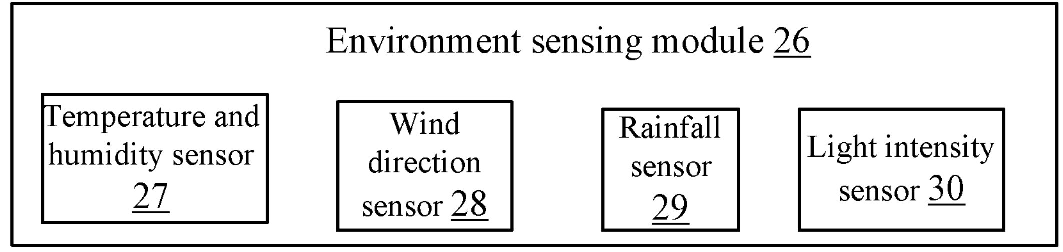
FIG. 7 is a schematic structural diagram of an environment sensing module.

FIG. 4 is a schematic flowchart of a method for monitoring farmland nitrogen leaching according to a specific implementation of the present disclosure. As shown in the figure, the present disclosure further provides a method for monitoring farmland nitrogen leaching. The method includes the following steps.

A. A cloud platform sends information about a to-be-measured site and a to-be-measured depth to a monitoring robot.

B. The monitoring robot moves to the to-be-measured site to be connected a leachate collection module at the to-be-measured depth of the to-be-measured site, extracts a leachate of the leachate collection module, performs leachate nitrogen detection on the leachate, and sends a leachate nitrogen detection result to the cloud platform.

Specifically, in FIG. 4, in a specific implementation of the present disclosure, the method for monitoring farmland nitrogen leaching includes the following steps.

S1. The monitoring robot receives the information about the to-be-measured site and the to-be-measured depth of the cloud platform through a narrowband Internet of Things (NB-IoT) communication module.

S2. The monitoring robot drives a movable carrier to move to a position of the to-be-measured site according to a command of a path planning unit of the cloud platform.

S3. A leachate transmission unit of the monitoring robot is connected to a leachate collection module at the to-be-measured depth of the to-be-measured site.

S4. The monitoring robot controls the leachate transmission unit to extract a leachate from the leachate collection module at the to-be-measured depth of the to-be-measured site, and adjusts a speed of extracting the leachate.

S5. After extracting the leachate, the monitoring robot sends an electromagnetic valve module close command to a Zigbee® module of the leachate collection module through a Zigbee® base station module, and starts to open a leachate nitrogen detection module to perform leachate nitrogen detection.

S6. The monitoring robot determines whether the to-be-measured site has another to-be-measured depth, and if the to-be-measured site has another to-be-measured depth, the monitoring robot repeats step 3 to step 5 until leachate extraction and nitrogen analysis at all the to-be-measured depths of the site are completed. In addition, the monitoring robot obtains environment information collected by an environment sensing unit through an environment sensing control unit, and finally uploads the obtained environment information, leachate nitrogen information, the to-be-measured site and depth coordinate information to the cloud platform.

S7. The farmland nitrogen leaching monitoring robot determines a to-be-measured site closest to the region from to-be-measured sites delivered by the cloud platform, and performs leachate nitrogen extraction and analysis and detection tasks again and repeats step 2 to step 7.

In addition, in the method for monitoring farmland nitrogen leaching in the specific implementation of the present disclosure, in step A, there are a plurality of to-be-measured sites sent by the cloud platform to the monitoring robot, and each to-be-measured site includes one or more to-be-measured depths; and in step B, the moving, by the monitoring robot, to the to-be-measured site for leachate extraction and leachate nitrogen detection includes:

after receiving the plurality of to-be-measured sites and information about one or more to-be-measured depths of each to-be-measured site, sending, by the leaching monitoring robot, a start command to a Zigbee® module of a leachate collection module at each to-be-measured depth of each to-be-measured site through a Zigbee® base station module, and detecting, by a leachate liquid level sensor of the leachate collection module at each to-be-measured depth of each to-be-measured site, a liquid level of a leachate collected by a leachate collection system corresponding to the leachate collection module, and sending the liquid level of the leachate collected by the leachate collection system corresponding to the leachate collection module to the leaching monitoring robot according to a predetermined period through the Zigbee® module at each to-be-measured depth of each to-be-measured site; and dynamically planning, a dynamical path planning unit of the leaching monitoring robot, a detection moving track of the monitoring robot according to a liquid level of a leachate collected by each leachate collection system, a position relationship among the to-be-measured site, and a quantity of to-be-measured depths of each to-be-measured site and according to each predetermined period; and performing, by the monitoring robot, leachate extraction and leachate nitrogen detection at each to-be-measured site and each to-be-measured depth according to the dynamically planned detection moving track.

The present disclosure has the following technical effects.

1. According to the farmland nitrogen leaching monitoring robot and method in the present disclosure, a large-range multi-point underground leachate can be automatically obtained and intelligently detected and analyzed.
2. The leaching monitoring robot in the present disclosure can perform autonomous navigation and move to each to-be-measured site to perform leachate collection and leachate nitrogen analysis, so that one or more leachate nitrogen analysis apparatuses do not need to be designed at each to-be-measured site, and each to-be-measured site shares one monitoring robot, so as to ensure consistency of leachate nitrogen analysis at each to-be-measured depth of each to-be-measured site and, avoid individual difference between each test device, thereby improving accuracy. In addition, the costs of the entire system can be reduced, and investment of a large quantity of leachate nitrogen analysis apparatuses can be avoided. In addition, because each leachate nitrogen analysis apparatus needs to report test result information to the cloud platform, but in the present disclosure, all tasks are uniformly completed by the monitoring robot, so that power consumption can be saved, and circuit wiring for each test site can be avoided.
3. The leaching monitoring robot in the present disclosure adopts a micro-fluidic technology before a leachate nitrogen detection module, so that a nitrogen component in a leachate can be detected by extracting a small amount of leachate, thereby avoiding consumption of a large amount of time for extracting a large amount of leachate for nitrogen measurement at a plurality of to-be-measured depths of a plurality of to-be-measured sites.
4. According to the robot system and method for monitoring farmland nitrogen leaching, quick collection, detection, and analysis of a plurality of leaching monitoring nodes on a large range can be implemented. Unattended monitoring can be implemented by setting a base station control program. A small amount of leachate is collected by using the micro-fluidic module. The costs are low, a detection time is short, efficiency is high, and a degree of automation and intelligence is high.
5. In particular, to further improve test efficiency, according to the robot system and method for monitoring farmland nitrogen leaching in the present invention, a dynamic path planning method is also adopted. A detection moving track of the monitoring robot is dynamically planned according to a liquid level of a leachate collected by each leachate collection system, a position relationship among to-be-measured sites, and a quantity of to-be-measured depths of each to-be-measured site and according to each predetermined period without presetting the detection moving track. After each to-be-measured site is measured, a next to-be-measured site is dynamically calculated and path optimization is performed according to a step method, so as to avoid a waiting time for leachate collection at a to-be-measured site. Therefore, it greatly improves the entire system test efficiency of the robot system and method for monitoring farmland nitrogen leaching for a plurality of to-be-measured sites and a plurality of to-be-measured depths.

The above explanation shows and describes several preferred embodiments of the present disclosure. But as mentioned above, it should be understood that the present disclosure is not limited to the form disclosed herein, and the explanation should not be regarded as an exclusion of other embodiments. Various combinations, modifications and environments can be achieved through the above guides and technologies or knowledge in related fields within the scope of conception of the present disclosure described herein. Modifications and changes made by those skilled in the art without departing from the spirit and scope of the present disclosure should fall within the protection scope of the appended claims of the present disclosure.

What is claimed is:

1. A robot system for monitoring farmland nitrogen leaching, wherein the robot system comprises a cloud platform, a monitoring robot, and a leachate collection module, wherein the cloud platform is configured to send information about a to-be-measured site and a to-be-measured depth to the monitoring robot and receive measurement information of the monitoring robot; and the monitoring robot is configured to move to the to-be-measured site to be connected to the leachate collection module located at the to-be-measured depth of the to-be-measured site, extract a leachate collected by the leachate collection module, perform leachate nitrogen detection on the leachate, and send a leachate nitrogen detection result to the cloud platform;

wherein there are a plurality of to-be-measured sites, each to-be-measured site comprises one or more to-be-measured depths, the leachate collection module is provided at each to-be-measured depth of each to-be-measured site, and the leachate collection module comprises a leachate collection system, a leachate liquid level sensor, an electromagnetic valve module, a transmission branch pipeline, and a wireless ad hoc network module; and the monitoring robot comprises a wireless ad hoc network base station module and a dynamical path planning unit;

after receiving the plurality of to-be-measured sites and information about one or more to-be-measured depths of each to-be-measured site from the cloud platform, the monitoring robot sends a start command to the wireless ad hoc network module of the leachate collection module at each to-be-measured depth of each to-be-measured site through the wireless ad hoc network base station module, and the leachate liquid level sensor of the leachate collection module at each to-be-measured depth of each to-be-measured site detects a liquid level of a leachate collected by the leachate collection system corresponding to the leachate collection module, and sends the liquid level of the leachate collected by the leachate collection system corresponding to the leachate collection module to the monitoring robot according to a predetermined period through the wireless ad hoc network module at each to-be-measured depth of each to-be-measured site; and the dynamical path planning unit of the monitoring robot dynamically plans a first detection moving track of the monitoring robot according to the liquid level of the leachate uploaded by each leachate collection system, a position relationship among the to-be-measured sites, and a quantity of to-be-measured depths of each to-be-measured site and according to each predetermined period;

and the monitoring robot is capable of performing leachate extraction and leachate nitrogen detection at each to-be-measured site and each to-be-measured depth according to the first detection moving track dynamically planned.

2. The robot system for monitoring farmland nitrogen leaching according to claim 1, wherein the cloud platform comprises a path planning unit, and the path planning unit plans a detection moving track of the monitoring robot according to a position relationship among the plurality of to-be-measured sites and a quantity of to-be-measured depths of each to-be-measured site, and sends the detection moving track to the monitoring robot;

and the monitoring robot receives the detection moving track, and is capable of sequentially performing leachate nitrogen detection at each to-be-measured site and each to-be-measured depth according to the detection moving track.

3. The robot system for monitoring farmland nitrogen leaching according to claim 1, wherein the leachate collection module is provided at the to-be-measured depth of the to-be-measured site, and the leachate collection module comprises a leachate collection system, an electromagnetic valve module, a transmission branch pipeline, and the wireless ad hoc network module; and the leachate collection system is configured to collect a leachate at the to-be-measured depth of the to-be-measured site, the electromagnetic valve module is connected to the leachate collection system and the transmission branch pipeline, and the wireless ad hoc network module is connected to the electromagnetic valve module and is connected to the wireless ad hoc network base station module of the monitoring robot in a wireless communication manner and is configured to open or close the electromagnetic valve module according to an instruction sent by the wireless ad hoc network base station module.

4. The robot system for monitoring farmland nitrogen leaching according to claim 3, wherein the monitoring robot comprises the wireless ad hoc network base station module, a leachate pipeline docking module, and a leachate extraction driving module; the to-be-measured site comprises one or more to-be-measured depths, and the leachate collection module is provided at each to-be-measured depth, and the leachate collection module comprises the leachate collection system, the electromagnetic valve module, the transmission branch pipeline, and the wireless ad hoc network module; and the monitoring robot comprises the wireless ad hoc network base station module that is in wireless connection with the wireless ad hoc network module of the leachate collection module at each to-be-measured depth, and the leachate pipeline docking module that is connected to the transmission branch pipeline of the leachate collection module at each to-be-measured depth; the monitoring robot communicates with the wireless ad hoc network module of the leachate collection module at each to-be-measured depth through the wireless ad hoc network base station module, to open the electromagnetic valve module of the leachate collection module at each to-be-measured depth, extract the leachate from the transmission branch pipeline of the leachate collection module at each to-be-measured depth, and perform nitrogen detection on the leachate extracted at each to-be-measured depth; and when a leachate at one to-be-measured depth is extracted, only the electromagnetic valve module of the leachate collection module at the to-be-measured depth is opened, and the electromagnetic valve module of the leachate collection module at another to-be-measured depth is kept in a closed state.

5. The robot system for monitoring farmland nitrogen leaching according to claim 4, wherein the monitoring robot comprises a reaction module, a micro-fluidic module, a leachate nitrogen detection module, a cleaning module, a waste liquid processing module, and a data processing module, the reaction module adds a to-be-reacted chemical reagent to the extracted leachate, and supplies a mixture of the chemical reagent and the leachate to the micro-fluidic module and then to the leachate nitrogen detection module for leachate nitrogen detection, the cleaning module is configured to clean the reaction module, the micro-fluidic module, and the leachate nitrogen detection module in the monitoring robot through cleaning liquid after leachate nitrogen detection is completed once, and the waste liquid processing module is configured to discharge the mixture of the chemical reagent and the leachate and the cleaning liquid.

6. The robot system for monitoring farmland nitrogen leaching according to claim 1, wherein the monitoring robot comprises a movable module, the movable module comprises a navigation module, a movable carrier, and a movable carrier driving unit, the navigation module is configured to obtain a position of the monitoring robot, the movable carrier comprises a wheel-type movable platform and a motor, and the movable carrier driving unit is configured to control a traveling direction and distance of the movable carrier.

7. The robot system for monitoring farmland nitrogen leaching according to claim 1, wherein the monitoring robot comprises an environment sensing module, the environment sensing module comprises a temperature and humidity sensor, a wind direction sensor, a rainfall sensor, and a light intensity sensor, and the monitoring robot sends information about a temperature, humidity, a wind direction, a rainfall, and light intensity collected by the environment sensing module to the cloud platform together with the leachate nitrogen detection result.

8. A method for monitoring farmland nitrogen leaching, comprising the following steps:

A: sending, by a cloud platform, information about a to-be-measured site and a to-be-measured depth to a monitoring robot; and B: moving, by the monitoring robot, to the to-be-measured site to be connected to a leachate collection module at the to-be-measured depth of the to-be-measured site, extracting a leachate of the leachate collection module, performing leachate nitrogen detection on the leachate, and sending a leachate nitrogen detection result to the cloud platform;

wherein in step A, there are a plurality of to-be-measured sites sent by the cloud platform to the monitoring robot, and each to-be-measured site comprises one or more to-be-measured depths; and in step B, the moving, by the monitoring robot, to the to-be-measured site for leachate extraction and leachate nitrogen detection comprises:

after receiving the plurality of to-be-measured sites and information about one or more to-be-measured depths of each to-be-measured site from the cloud platform, sending, by the monitoring robot, a start command to a wireless ad hoc network module of a leachate collection module at each to-be-measured depth of each to-be-measured site through a wireless ad hoc network base station module, and detecting, by a leachate liquid level sensor of the leachate collection module at each to-be-measured depth of each to-be-measured site, a liquid level of a leachate collected by a leachate collection system corresponding to the leachate collection module, and sending the liquid level of the leachate collected by the leachate collection system corresponding to the leachate collection module to the monitoring robot according to a predetermined period through the wireless ad hoc network module at each to-be-measured depth of each to-be-measured site; and dynamically planning, by a dynamical path planning unit of the monitoring robot, a first detection moving track of the monitoring robot according to a liquid level of a leachate collected by each leachate collection system, a position relationship among the to-be-measured sites, and a quantity of to-be-measured depths of each to-be-measured site and according to each predetermined period;

and performing, by the monitoring robot, leachate extraction and leachate nitrogen detection at each to-be-measured site and each to-be-measured depth according to the first detection moving track dynamically planned.

* * * * *